(12) United States Patent
Hama et al.

(10) Patent No.: US 7,422,356 B2
(45) Date of Patent: Sep. 9, 2008

(54) LIGHT EMITTING DEVICE

(75) Inventors: Atsutomo Hama, Anan (JP); Yukihiro Hayashi, Anan (JP)

(73) Assignee: Nichia Corporation, Anan-shi (JP)

( * ) Notice: Subject to any disclaimer, the term of this patent is extended or adjusted under 35 U.S.C. 154(b) by 278 days.

(21) Appl. No.: 11/449,719

(22) Filed: Jun. 9, 2006

(65) Prior Publication Data

US 2006/0279950 A1   Dec. 14, 2006

(30) Foreign Application Priority Data

Jun. 13, 2005 (JP) ............................. 2005-172220
May 8, 2006 (JP) ............................. 2006-129332

(51) Int. Cl.
*F21V 33/00* (2006.01)

(52) U.S. Cl. .................... 362/574; 362/129; 362/84; 362/572; 362/553; 362/580; 600/129

(58) Field of Classification Search ............... 362/574, 362/575, 572, 580, 558, 553, 84; 600/129
See application file for complete search history.

(56) References Cited

U.S. PATENT DOCUMENTS

| 4,572,609 | A | | 2/1986 | Sakuragi et al. |
| 4,678,273 | A | | 7/1987 | Vilhelmsson et al. |
| 4,693,556 | A | * | 9/1987 | McCaughan, Jr. ......... 427/163.2 |
| 4,695,697 | A | * | 9/1987 | Kosa ..................... 219/121.83 |
| 5,807,389 | A | * | 9/1998 | Gardetto et al. ............... 606/17 |
| 6,260,614 | B1 | | 7/2001 | Guy |
| 2005/0031281 | A1 | | 2/2005 | Nath |
| 2005/0084229 | A1 | | 4/2005 | Babbitt et al. |

FOREIGN PATENT DOCUMENTS

| EP | 1605199 A2 | 12/2005 |
| JP | H08-043659 A | 2/1996 |
| JP | 2005-205195 A | 8/2005 |
| JP | 2005-328921 A | 12/2005 |
| JP | 2005-332989 A | 12/2005 |
| JP | 2006-61685 A | 3/2006 |
| WO | WO-01-40702 A1 | 6/2001 |

* cited by examiner

*Primary Examiner*—Laura Tso
(74) *Attorney, Agent, or Firm*—Global IP Counselors, LLP

(57) ABSTRACT

A light emitting device, comprises at least: a light emitting element; a wavelength conversion member for converting the wavelength of light from the light emitting element; a bendable light guide member for guiding light from the light emitting element to the wavelength conversion member; and a heat conduction member that is thermally connected to the wavelength conversion member.

6 Claims, 14 Drawing Sheets

Fig.13d

LIGHT EMITTING DEVICE

BACKGROUND OF THE INVENTION

1. Field of the Invention

The present invention relates to a light emitting device having a light emitting element, a light guide member, and a wavelength conversion member.

2. Description of the Related Art

There has long been a need for a light emitting device with which color information can be accurately reproduced at high output. The use of light emitting diodes (hereinafter referred to as LEDs), laser diodes (hereinafter referred to as LDs), and other such light emitting elements as the light source for such devices has already been proposed (see, for example, WO01/040702).

LEDs and LDs are compact, have good power efficiency, emit light in vivid colors, and eliminate problems such as broken bulbs. In particular, LDs have higher optical density than LEDs, so a light emitting device of higher brightness can be obtained.

Nevertheless, with the LEDs, LDs, and so forth discussed in WO01/040702, when light is emitted from an LED or LD to the outside via a wavelength conversion member, the wavelength conversion member is degraded by heat originating in the light, so that light from the light emitting element can no longer be fully emitted to the outside, or in some cases, the wavelength conversion member becomes discolored and makes the light emitting device unusable, among other such problems.

SUMMARY OF THE INVENTION

The present invention is intended to solve the above problems, and it is an object thereof to provide a light emitting device with high output and a long service life.

The present invention provides a light emitting device, comprising at least: a light emitting element; a wavelength conversion member for converting the wavelength of light from the light emitting element; a bendable light guide member for guiding light from the light emitting element to the wavelength conversion member; and a heat conduction member that is thermally connected to the wavelength conversion member.

DESCRIPTION OF THE PREFERRED EMBODIMENTS

Figure 1:
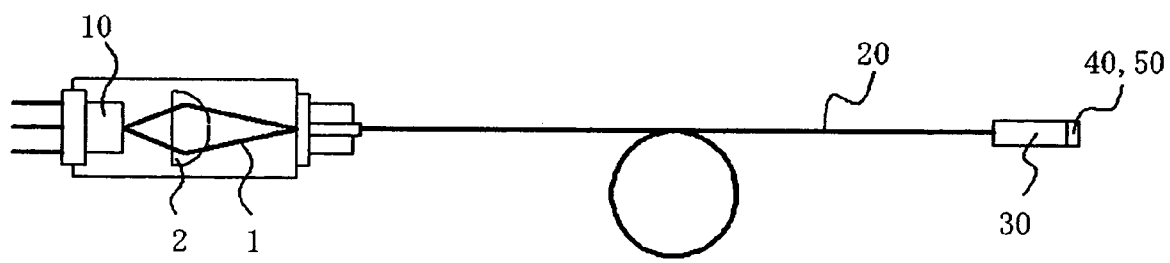
FIG. 1 is simplified overall diagram of the light emitting device of the present invention.

The light emitting device of the present invention will now be described through reference to the drawings. However, the light emitting devices discussed below are merely given to embody the technological concept of the present invention, and the present invention is not limited thereto. Unless otherwise specified, the dimensions, materials, shapes, relative layouts, and so forth of the constituent members are nothing more than illustrative examples, and should not be construed to limit the scope of the present invention to just these. Furthermore, the sizes, positional relationships, and so forth of the members shown in the drawings may be exaggerated in order to clarify the description. In addition, the elements that make up the present invention may be such that a plurality of elements are constituted by a single member, or conversely, a single element may be constituted by a plurality of members.

FIG. 1 is simplified overall diagram of the light emitting device of the present invention, and FIG. 2 is a simplified diagram of the detailed structured near the distal end of the light emitting device of the present invention. As shown in FIGS. 1 and 2, the light emitting device of the present invention is made up primarily of a light emitting element 10, a light guide member 20, a wavelength conversion member 40, and a heat conduction member 50 that is thermally connected to the wavelength conversion member 40. This allows heat generated in the wavelength conversion member 40 by light from the light emitting element 10 to be effectively taken away by the heat conduction member 50, and mitigates the degradation and discoloration caused by heat to the wavelength conversion member 40 and its peripheral members.

In this Specification, the phrase "thermally connected" does not necessarily mean that one member is directly and completely connected physically to another member. For instance, one member may be indirectly connected with another member via yet another member, or one member may be partially in contact with another member.

Light Emitting Element

There are no particular restrictions on the light emitting element 10, but an LD or LED can be used favorably. Using one of these affords a light emitting device with excellent initial drive characteristics, good durability in terms of vibration and repeated on/off flashing, a compact size, and high light emission output.

In particular, since an LD has higher optical density than an LED, the use of an LD allows the brightness of the light emitting device to be easily increased, but this same high optical density also means that the wavelength conversion member 40 will be more apt to generate heat that can lead to degradation and discoloration. The present invention greatly reduces the adverse effect of heat from the wavelength conversion member 40, and is therefore particularly effective when an LD is used as the light emitting element 10.

Light Guide Member

The light guide member 20 is designed to be bendable and to extend in the lengthwise direction. This allows light to be easily guided to the desired location. The light guide member 20 preferably has a circular cross section, but is not limited to this. There are no particular restrictions on the diameter of the light guide member 20, but it can be 3000 µm or less, 1000 µm or less, 400 µm or less, or even 200 µm or less. When the cross section is not circular, the "diameter" of the light guide member 20 refers to the average diameter in the cross section.

The light emitting element 10 is disposed at one end of the light guide member 20, and the wavelength conversion member 40 is disposed at the other end. There are no particular restrictions on the light guide member 20, as long as it guides light from the light emitting element 10 to the wavelength conversion member 40, but an optical fiber can be used to advantage. An optical fiber is preferable because it can guide light from the light emitting element very efficiently. An optical fiber is usually configured such that a core with a high refractive index is disposed on the inside, and cladding with a low refractive index is disposed on the outside. There are no particular restrictions on the shape of the end of the light guide member 20 on the light emitting element 10 side and/or the end on the wavelength conversion member 40 (discussed below) side, and any of various shapes can be employed, such as a flat surface, a convex lens, a concave lens, or a shape in which bumps are provided in at least some portion. For instance, when the light guide member 20 is an optical fiber, the core and/or cladding at the ends can have one of the above-mentioned shapes.

Covering Member

The light emitting device of the present invention can be equipped with a covering member 30. The covering member 30 covers at least part of the side face of the light guide member 20, and preferably the side face of (that is, around) the emission-side end. Providing the covering member 30 allows the wavelength conversion member 40, the heat conduction member 50 (discussed below), and so forth to be disposed more easily.

When the light emitting device of the present invention is equipped with the covering member 30, the covering member 30 is preferably connected thermally to the wavelength conversion member 40 via a heat conduction member 50. This allows heat generated by the wavelength conversion member 40 to be more effectively radiated to the covering member 30, which mitigates the adverse effects of heat from the wavelength conversion member 40. Here, if the thermal conductivity of the covering member 30 is made to be higher than the thermal conductivity of the wavelength conversion member 40, degradation and discoloration of the wavelength conversion member 40 caused by heat can be more effectively reduced.

The covering member 30 is preferably formed from a material that has either high thermal conductivity, or a high optical refractive index, or a high reflectivity with respect to excited light from the light emitting element and/or light that has undergone wavelength conversion (discussed below), or a material that has two or more of these properties. An example of such a material is one whose reflectivity is at least 80% with respect to excited light and/or light that has undergone wavelength conversion, whose refractive index is at least n:1.4 with respect to light of about 350 to 500 nm, and/or whose thermal conductivity is at least 0.1 W/m·° C.

The covering member 30 can, for example, be made of silver (Ag), aluminum (Al), copper (Cu), nickel (Ni), silicon carbide (SiC), zirconia ($ZrO_2$), alumina ($Al_2O_3$), aluminum nitride (AlN), barium sulfate ($BaSO_4$), carbon, stainless steel, borosilicate glass, or the like. Of these, zirconia is preferable because it has high reflectivity and is easy to work. Furthermore, because alumina has high thermal conductivity and high reflectivity over the entire visible light spectrum, it is particularly favorable when the light emitting device is one that emits white light.

A light reflecting film may be disposed on the side of the covering member 30 where the wavelength conversion member 40 is disposed, or specific bumps may be formed on this side so that light is scattered. As a result, when light from the light emitting element and/or light that has undergone wavelength conversion is returned by reflection to the light guide member 20 side, it can be re-reflected by the covering member 30, and light from the light emitting element and/or light that has undergone wavelength conversion can be taken off to the outside more effectively. The side having the light reflecting film and/or bumps need not be provided to just the covering member 30, but may also be provided to at least part of the emission end of the light guide member 20.

Figure 8A:
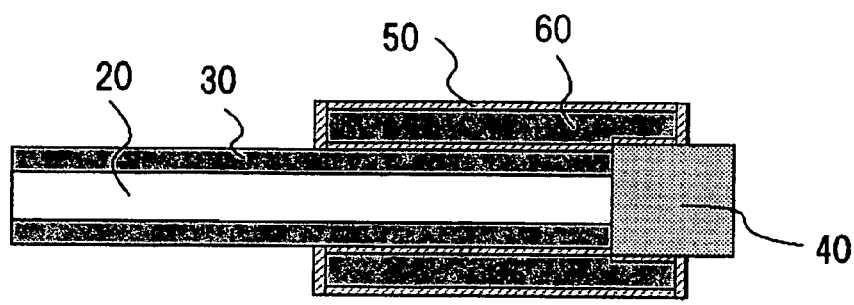

Also, the covering member 30 need not necessarily be a single member, and a combination of a plurality of members of various shapes may be used (see FIG. 8aa, for example). In this case, the covering member 30 can be given the function of supporting the light guide member 20 and the wavelength conversion member 40, or the finction of a reflector for reflecting light, or the function of sandwiching a heat conduction member (discussed below) in between members.

Wavelength Conversion Member

The wavelength conversion member 40 converts the wavelength of light from the light emitting element 10, and may, for example, be made up solely of a fluorescent material, or a fluorescent material may be contained in a translucent member such as an epoxy resin, silicone resin, or other such organic material, or a low-melting point glass, crystalline glass, or other such inorganic material. In particular, when a translucent member made of an organic material is used, since this member will be susceptible to degradation by light, the present invention is particularly effective when the translucent member is made of an organic material.

The wavelength conversion member 40 absorbs at least part of the light from the light emitting element 10, converts the wavelength to a different wavelength band, and emits light having an emission spectrum in the red band, the green band, the blue band, etc. There are no particular restrictions on the type of fluorescent material, as long as it will at least convert the wavelength of light from the light emitting element, and various kinds can be used. With the light emitting device of the present invention, for example, light from the light emitting element 10 can be mixed with light from one or more fluorescent materials, or light from two or more fluorescent materials can be mixed, allowing a white color to be obtained. To obtain better color rendering, it is preferable to use a material with which the average color rendering index (Ra) of incident light will be at least 70, with at least 80 being even better.

The wavelength conversion member 40 can contain $SiO_2$ or another such filler as desired in the present invention. A filler serves to reflect and scatter incident light. This results in better color mixing and reduces color unevenness. Also, mixing a filler into the wavelength conversion member 40 allows the viscosity thereof to be adjusted, so it can be more easily disposed in the light guide member 20, the covering member 30, and the heat conduction member 50.

The wavelength conversion member 40 may consist of a first layer constituted by an inorganic member containing a fluorescent material, a second layer constituted by an organic member containing the same or a different type of fluorescent material as the fluorescent material contained in the first layer, and so forth, disposed in that order starting from the light emitting element 10 side. This reduces degradation of the first layer, which is nearer to the light emitting element 10 that is relatively more prone to degradation, and as a result increases the service life of the light emitting device. A translucent member that does not contain a fluorescent material may also be used in combination at the desired location within the wavelength conversion member. For instance, the wavelength conversion member 40 shown in FIGS. 2a to 9ii may be partially formed solely from a translucent member a translucent member that does not contain a fluorescent material.

In general, some of the light will not undergo wavelength conversion and will become heat. With the present invention, because the portion where the light is guided to the wavelength conversion member is extremely narrow, there is pronounced concentration of light in the wavelength conversion member, and the attendant generation of heat, but the degradation and discoloration of the wavelength conversion member 40 can be effectively reduced even in this situation with the light emitting device of the present invention.

Heat Conduction Member

The heat conduction member 50 absorbs the heat produced by the wavelength conversion member 40, and also reduces the generation of heat in the wavelength conversion member 40. Also, it is preferably translucent so that at least part of the light from the light emitting element 10 and/or light that has undergone wavelength conversion will be transmitted. This allows light from the light emitting element 10 and/or light that has undergone wavelength conversion to be taken off from efficiently. There are no particular restrictions on the material constituting the heat conduction member 50, but one whose thermal conductivity is at least about 0.1 w/m·k is preferable, with at least about 0.5 w/m·k being even better. From another standpoint, it is preferable to use a material whose thermal conductivity is better than that of the organic member or inorganic member used in the wavelength conversion member. For example, aluminum nitride (AlN), silicon carbide (SiC), CuW, CuMO, Cu diamond, diamond, a transparent electroconductive material (such as indium tin oxide (ITO), indium oxide ($In_2O_3$), zinc oxide (ZnO), tin oxide ($SnO_2$), or magnesium oxide (MgO)), or the like can be used, either singly or in combination. Aluminum nitride is particularly favorable because it has relatively high thermal conductivity and is easy to mold into a light emitting device.

Figure 2A:
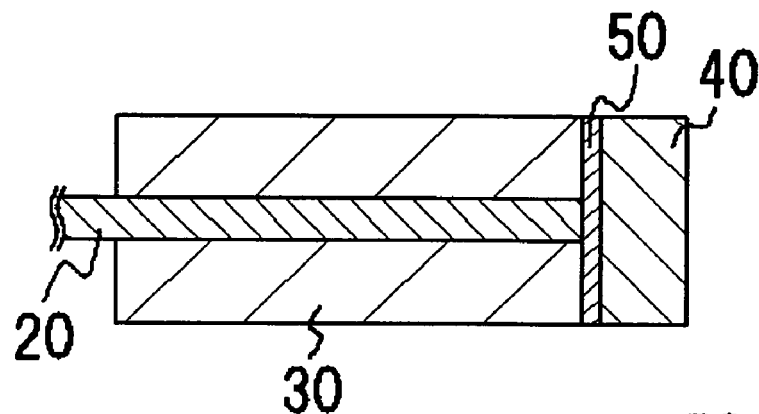
FIGS. 2 to 4 are simplified diagrams of the cross sectional structure near the distal end in the light emitting device of the present invention.
Figure 2B:
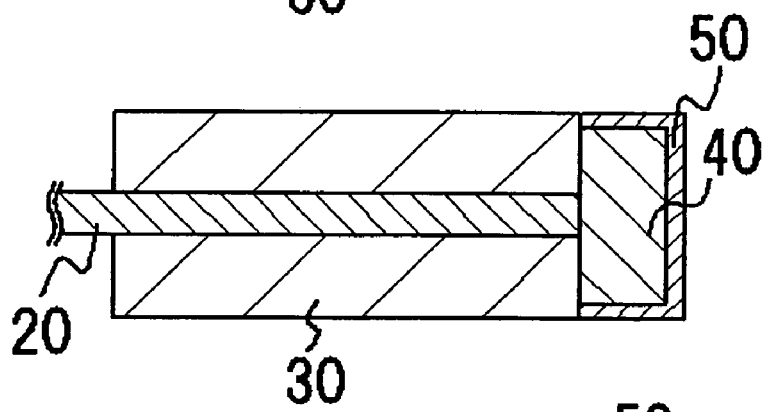
Figure 2C:
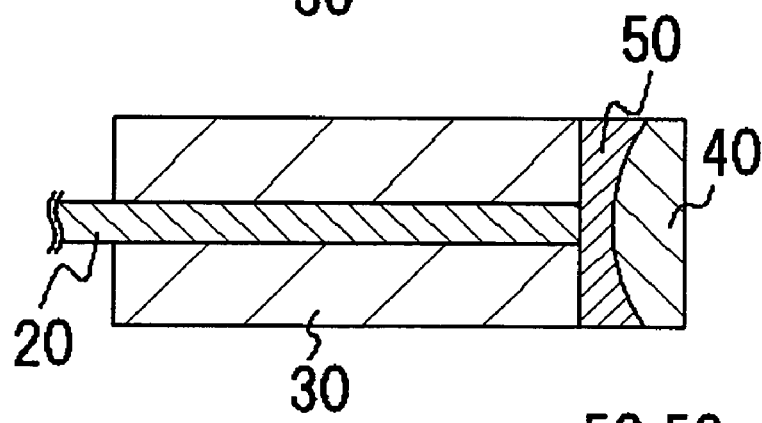
Figure 2D:
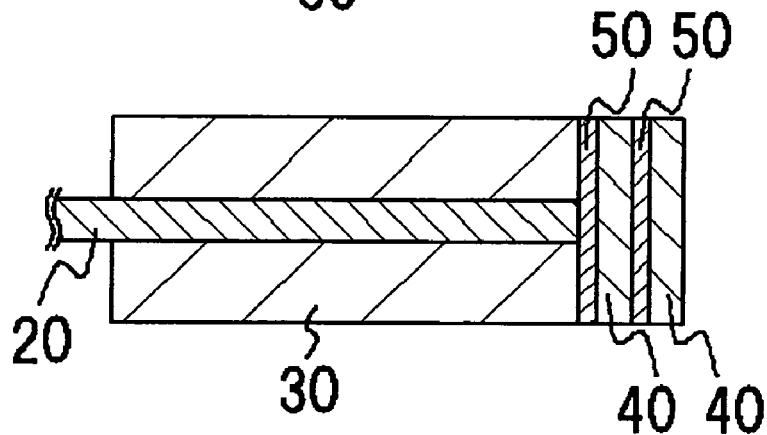
Figure 3E:
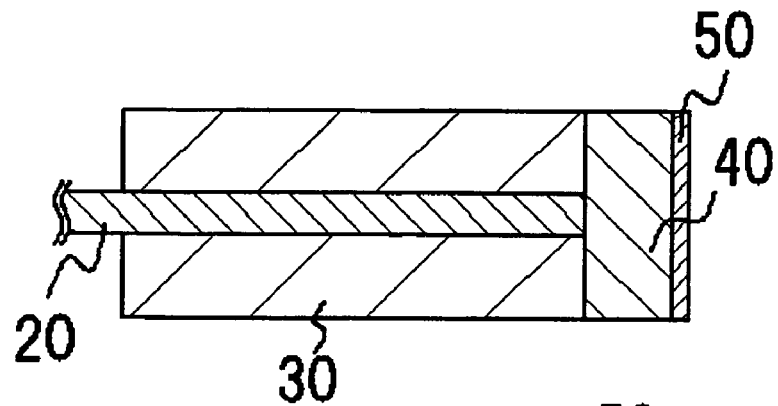
Figure 3F:
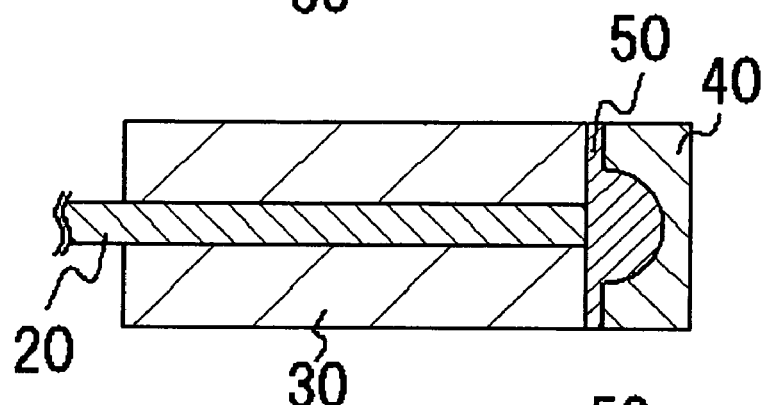
Figure 3G:
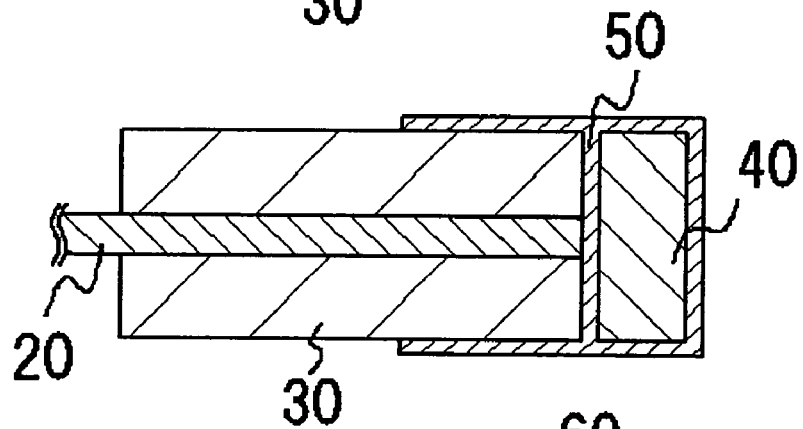
Figure 3H:
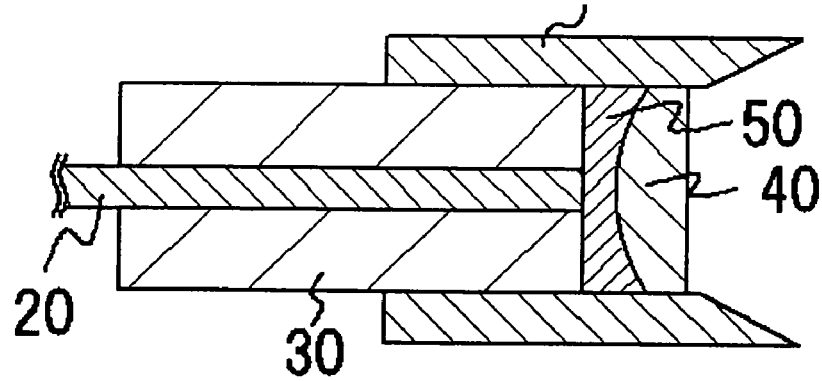
Figure 4I:
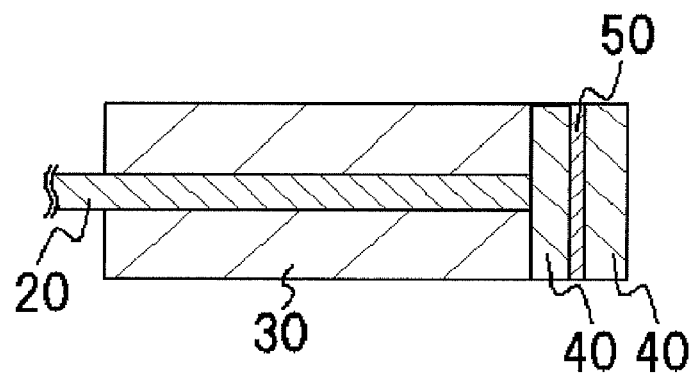
Figure 4J:
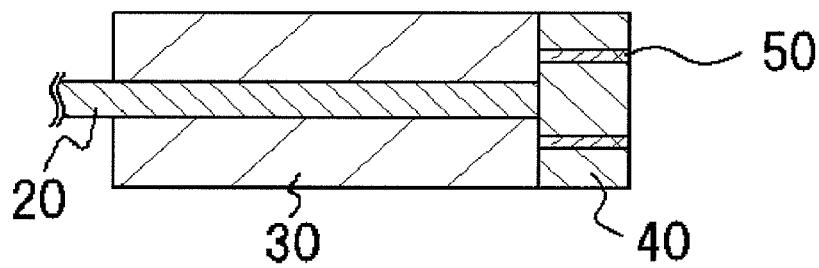
Figure 4K:
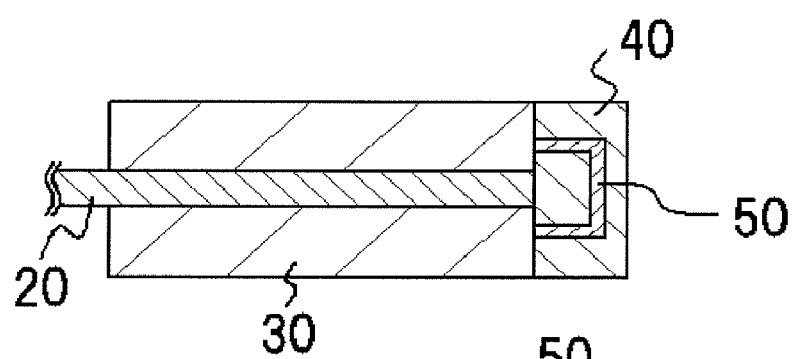
Figure 4L:
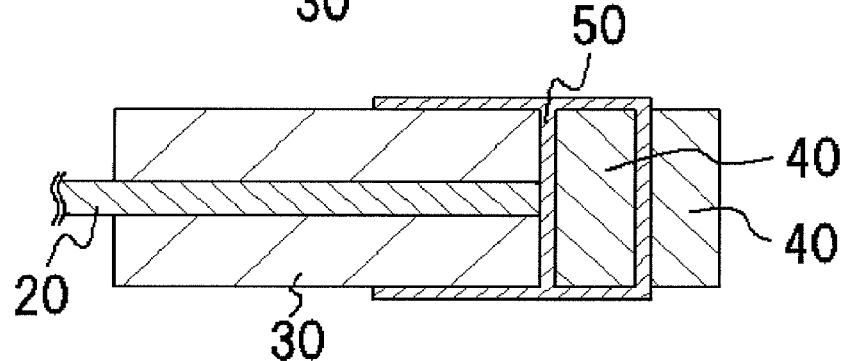
Figure 5M:
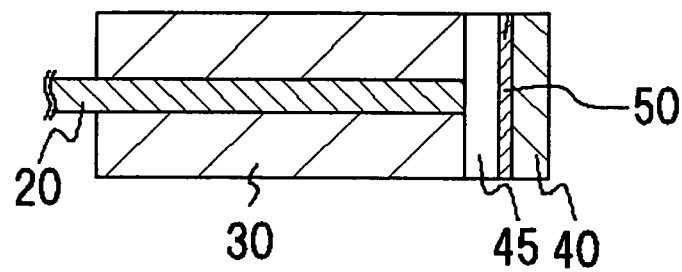
FIG. 5 is simplified diagrams of the cross sectional and oblique structure near the distal end in the light emitting device of the present invention.
Figure 5N:
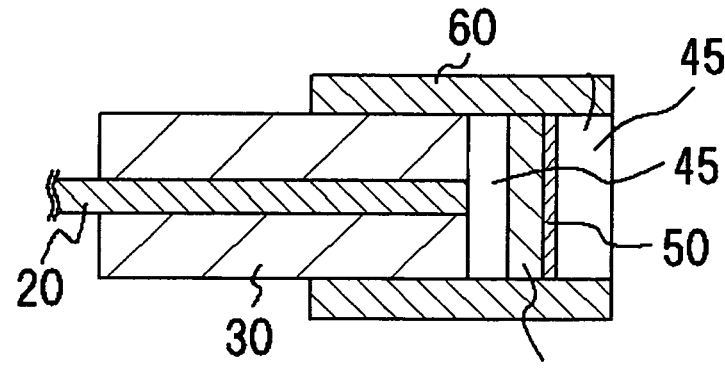
Figure 5O:
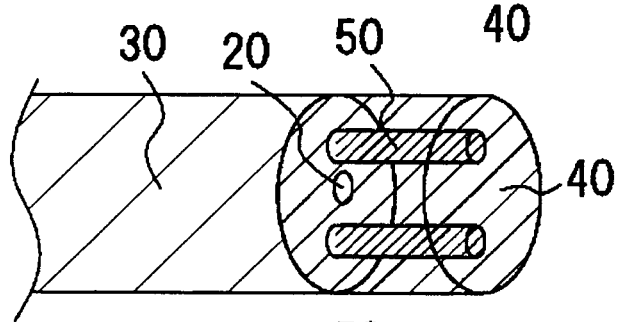
Figure 5P:
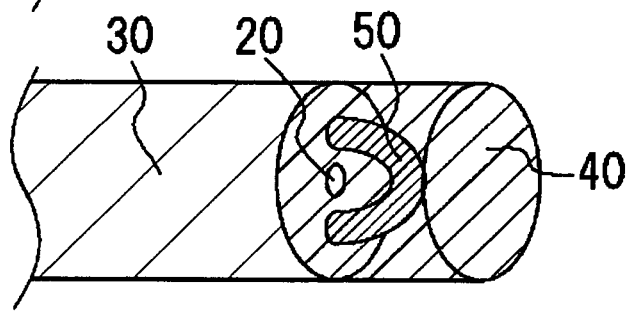
Figure 5Q:
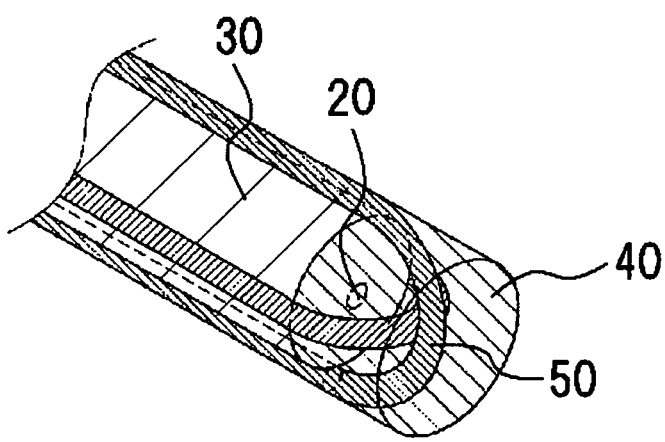
Figure 6R:
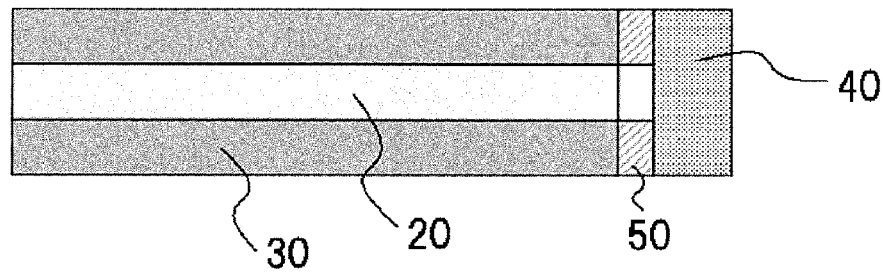
FIGS. 6 to 9 are simplified diagrams of the cross sectional structure near the distal end in the light emitting device of the present invention.
Figure 6S:
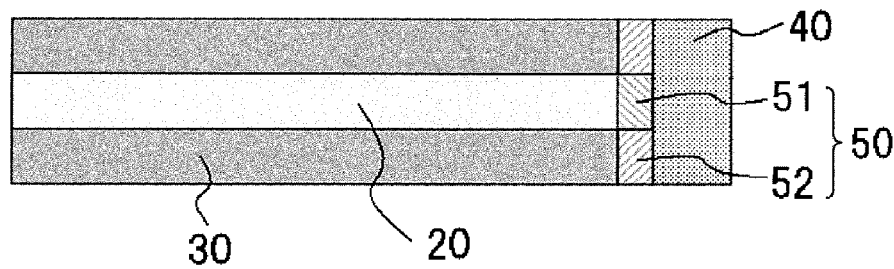
Figure 6T:
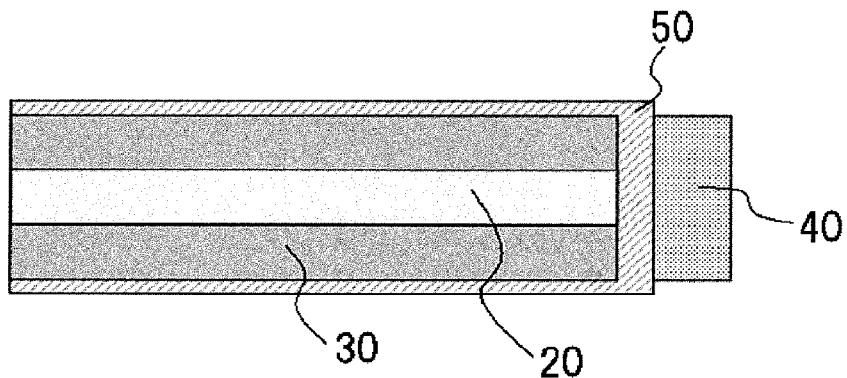
Figure 6U:
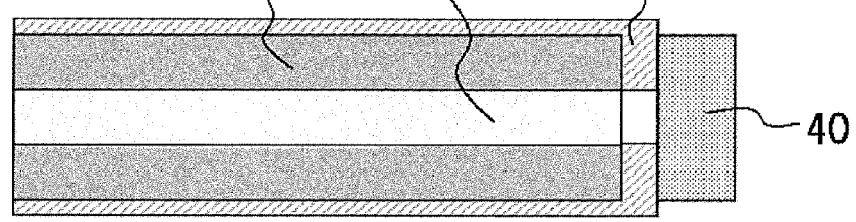
Figure 7V:
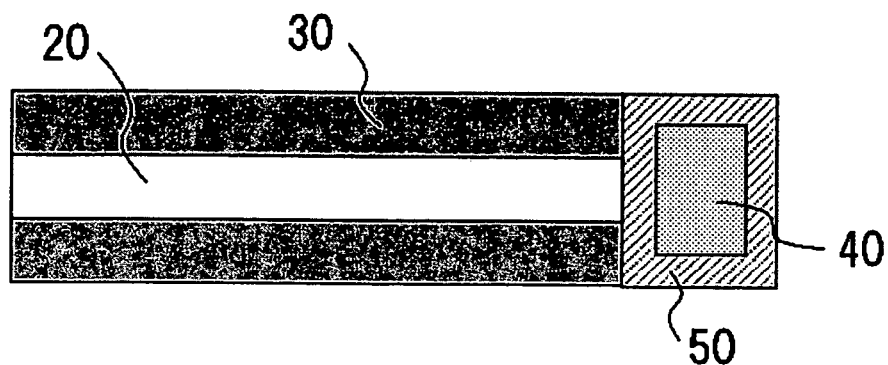
Figure 7X:
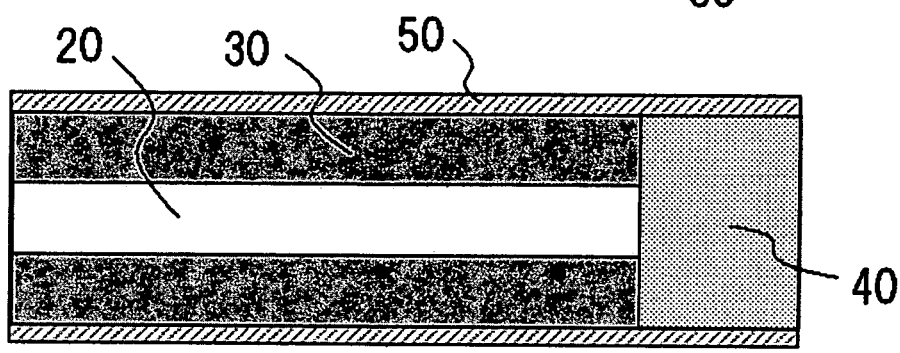
Figure 7Y:
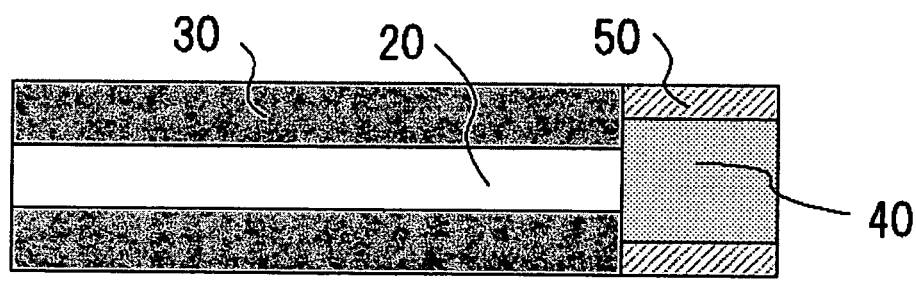
Figure 7Z:
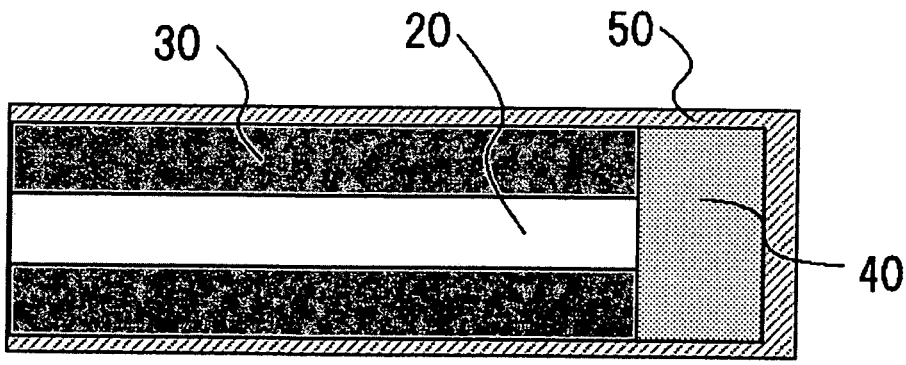
Figure 8B:
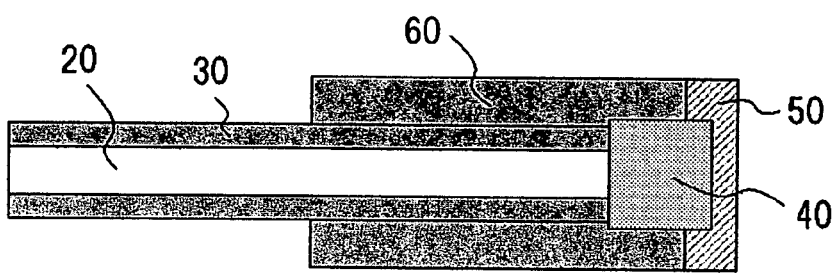
Figure 8C:
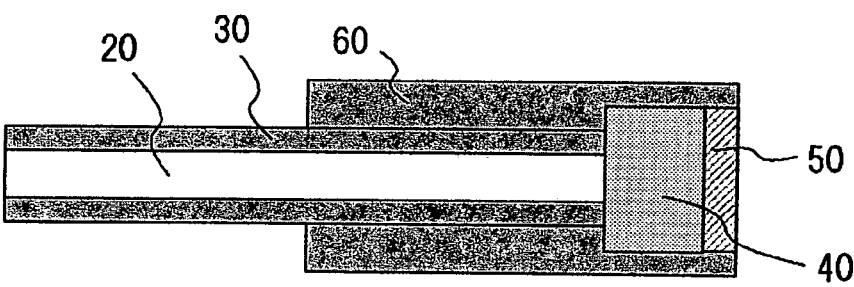
Figure 8D:
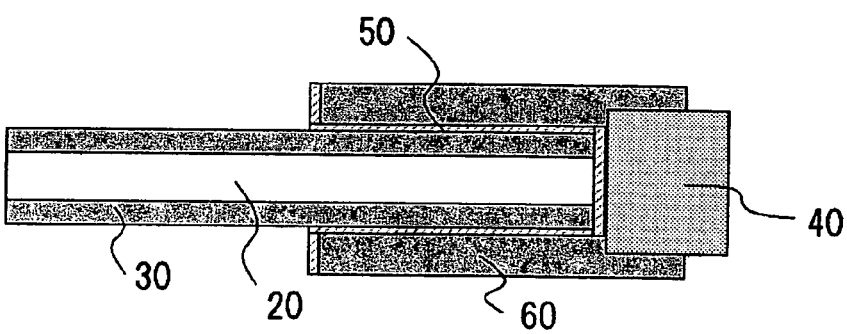
Figure 8E:
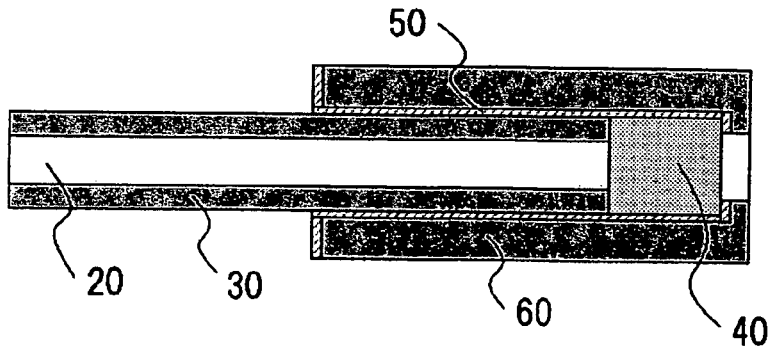

The heat conduction member 50 may, for example, be disposed between the light guide member 20 and the wavelength conversion member 40 as shown in FIGS. 2a, 2c, 2d, 3f to 3h, and 6s, or may be disposed on the opposite side of the wavelength conversion member 40 from the light guide member 20 as shown in FIGS. 3e, 8bb, and 8cc, or may be disposed so as to cover all or part of the surrounding part (the outer surface) of the wavelength conversion member 40 as shown in FIGS. 2b, 3g, 4i, 6t, 7v to 7z, and 9ff to 9ii, or two or more heat conduction members 50 may be disposed via the wavelength conversion member 40 as shown in FIGS. 2d and 4i, or may be disposed between the wavelength conversion member 40 and a translucent member 45 as shown in FIGS. 5m and 5n, or may be disposed in a concentric circular or cup shape in the wavelength conversion member 40 as shown in FIGS. 4j and 4k, or may be disposed in the form of rods or bent rods (the more, the better) in the wavelength conversion member 40 as shown in FIGS. 5o to 5q. The heat conduction member 50 may also be in the form of a mesh. The heat conduction member 50 may be disposed only between the wavelength conversion member 40 and the covering member 30 as shown in FIGS. 6r and 6u, or the heat conduction member 50 may be made up of a translucent material 51 and a reflective material 52 from the light guide member 20 to the covering member 30 as shown in FIG. 6s.

Figure 9F:
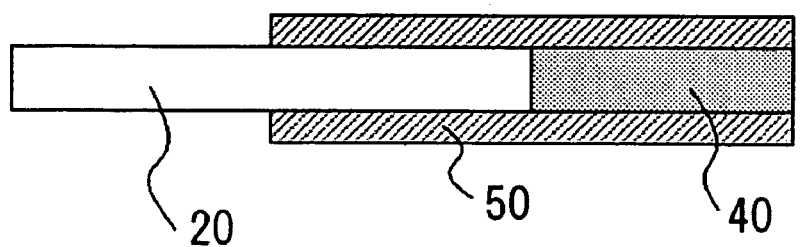
Figure 9G:
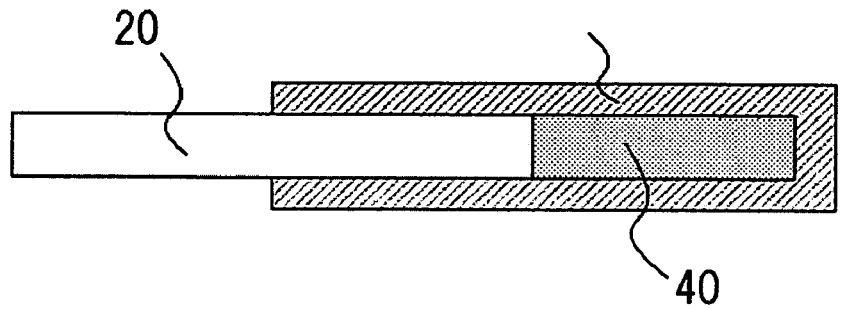
Figure 9H:
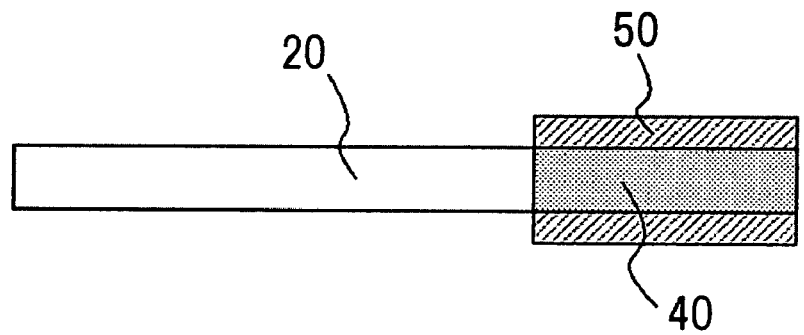
Figure 9I:
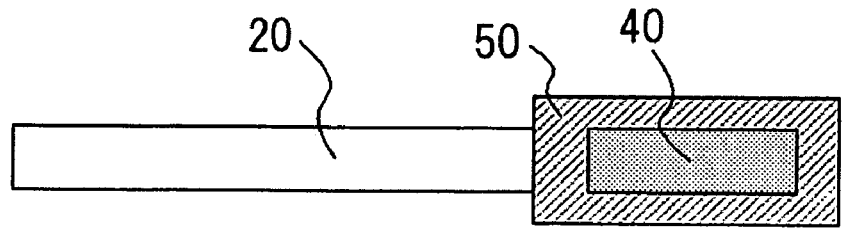

From another standpoint, as shown in FIGS. 8aa to 8ee, the heat conduction member 50 may be disposed so as to be sandwiched by a plurality of covering members 30. Further, the heat conduction member 50 may be disposed as shown in FIGS. 9ff to 9ii, without the covering member 30 being provided.

Also, the heat conduction member 50 can be in the form of a convex lens as shown in FIG. 3f, or in the form of a concave lens as shown in FIGS. 2c and 3h.

It is especially favorable for the contact surface area between the heat conduction member 50 and the wavelength conversion member 40 and/or the covering member 30 to be as large as possible because heat dissipation efficiency will be higher. It is also preferable for the configuration to be such that the heat conduction member 50 diffuses the light from the light guide member 20, as shown in FIG. 2c, etc., in which the heat conduction member 50 is a concave lens. This results in light of higher density from the light guide member 20 being incident on the wavelength conversion member 40 after first being diffused, rather than being incident directly, so less light is focussed on the wavelength conversion member 40, and degradation and discoloration of the wavelength conversion member 40 can be effectively reduced. Since the light guide member 20 is slender enough to be bendable, it has a relatively small diameter and light is more readily focussed. Therefore, a configuration in which the heat conduction member 50 diffuses light from the light guide member 20 is particularly effective when a bendable light guide member 20 is used. Also, as shown in FIG. 6s, the maximum heat dissipation characteristics can be attained, without lowering the output of light from the light emitting element, by disposing a translucent material at the light guide member 20 and a material with high thermal conductivity and reflectivity such as silver or another such metal) at the covering member 30.

As shown in FIGS. 2h, 5n, and 8aa to 8ee, heat dissipation can be further enhanced with the light emitting device of the present invention by disposing a metallic reflector, a wavelength conversion member supporting member, or other such second covering member 60 so as to be thermally connected with the heat conduction member 50.

When the heat conduction member 50 is a convex lens, a concave lens, or any other desired form, the area around the glass, resin, or the like can be covered with a material such as ITO to produce the heat conduction member 50. This allows the heat conduction member 50 to be produced in the desired form with relative ease. The covering of the material constituting the heat conduction member 50 can be accomplished by a known method, such as sputtering, vapor deposition, or plating.

The following methods are particularly favorable for disposing the heat conduction member 50 on just the outer surface of the covering member 30 as shown in FIGS. 6r and 6u.

Figure 13A:
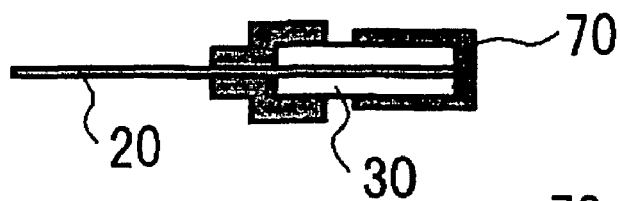
FIGS. 13 and 14 are simplified diagrams illustrating some of the steps involved in manufacturing the light emitting device of the present invention.

First, as shown in FIG. 13a, the end face on the emission side of the light guide member 20 and the covering member 30 attached to the end part on the emission side of the light guide member 20 are coated with a resist 70. The resist may be heating after this coating.

Figure 13B:
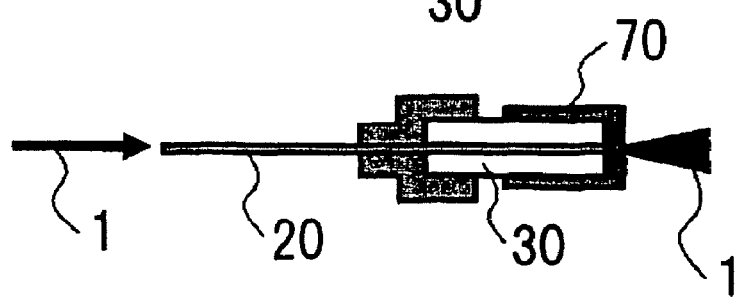
Figure 13C:
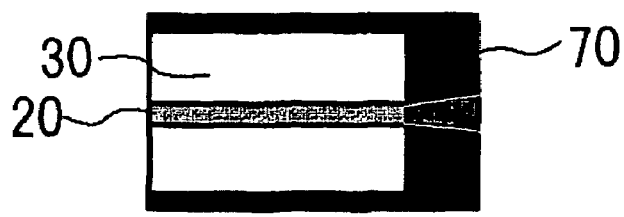

Next, as shown in FIG. 13b, light is allowed to propagate through the light guide member 20 to expose the resist 70 covering the emission-side end face of the light guide member 20. With this method, just the desired portion of the resist 70 can be exposed at high precision, without having to perform mask alignment (see FIG. 13c).

The resist 70 is then developed with an alkali solution and rinsed with water. This results in a pattern in which the resist 70 remains only at the emission-side end part of the light guide member 20.

Figure 13E:
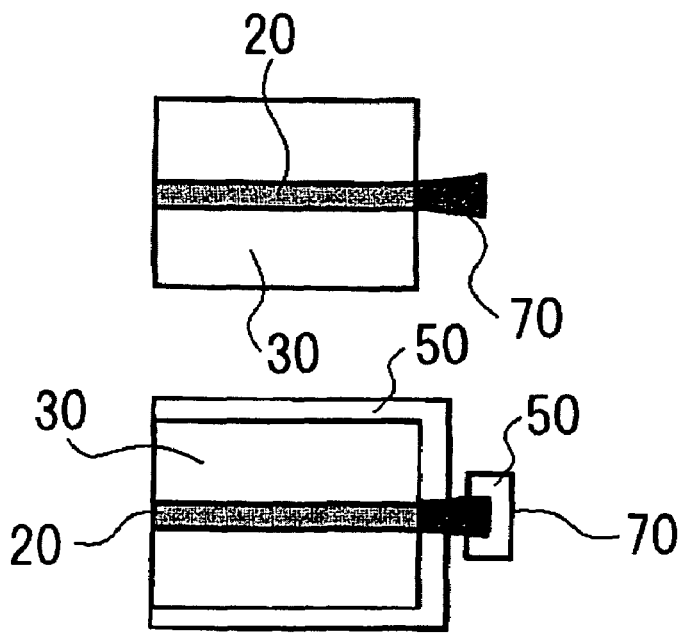
Figure 13F:
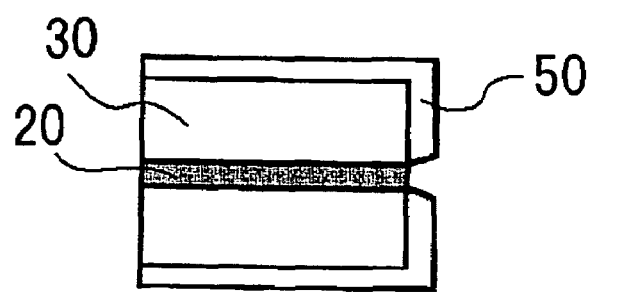

After this, as shown in FIG. 13e, a metal film is formed over the entire surface of the covering member 30 including the remaining resist 70, and the heat conduction member 50 consisting of the metal film is formed by lift-off on the surface of the covering member 30 other than the emission-side end part of the light guide member 20, as shown in FIG. 13f.

With this process, the use of a negative resist is favorable, but a positive resist may be used instead, and inverted exposure or another such method employed. Also, drying, ashing, or the like may be performed in the course of developing and rinsing with water.

Figure 14A:
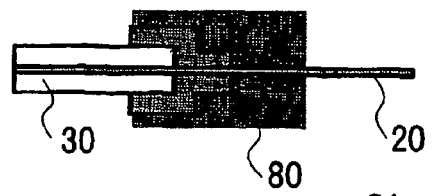

As another method, as shown in FIG. 14a, the heat conduction member may be formed as a plating film on the outer surface of the covering member 30 composed of an electroconductive material.

First, a mask 80 is formed so as to cover the portion of the covering member 30 that does not require plating.

Figure 14B:
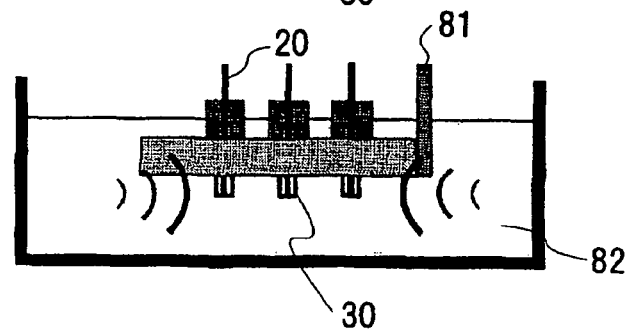

Next, as shown in FIG. 14b, the covering member 30 is fixed to a fixing member 81. The covering member 30 is preferably immersed in an ethanol solution 82 and subjected to ultrasonic degreasing and cleaning. This allows the plating of the surface of the covering member 30 to be performed more precisely.

Figure 14C:
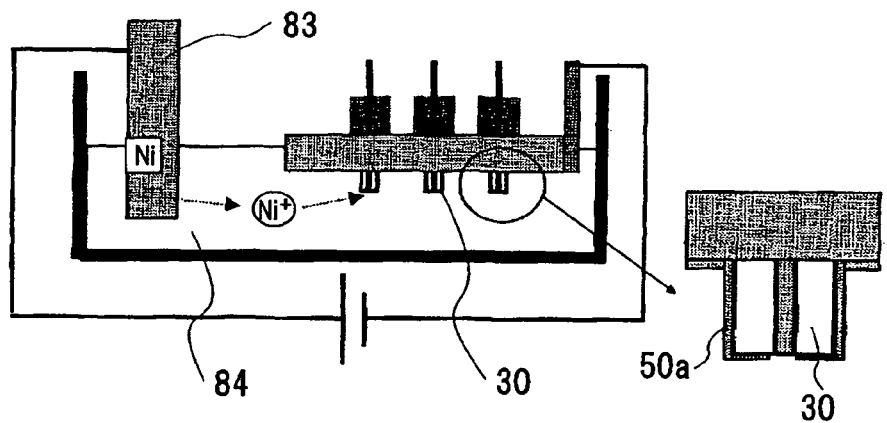

Next, as shown in FIG. 14c, the surface of the covering member 30 is subjected as desired to strike plating. For example, the covering member 30 and a nickel electrode 83 are immersed in a dilute hydrochloric acid solution, and current is supplied. This forms a metal film 50a on just the surface of the covering member 30 composed of the electroconductive material. This strike plating improves the quality of the plating film.

Figure 14D:
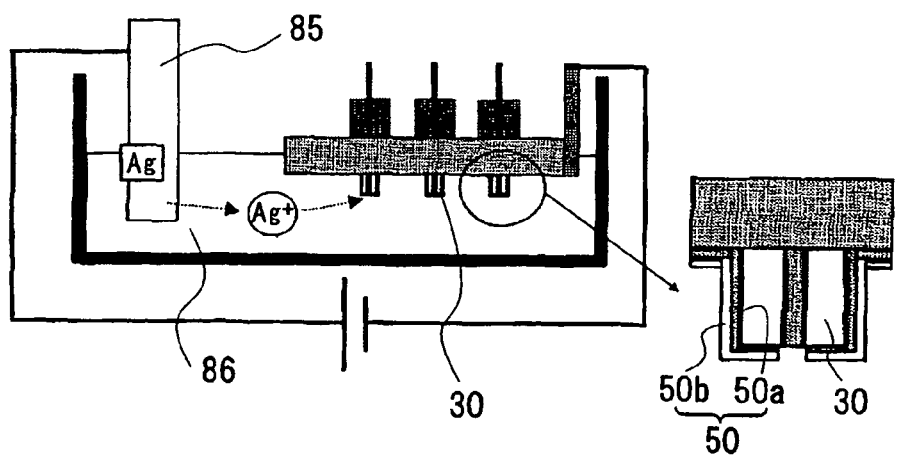

Next, the surface of the covering member 30 is plated as shown in FIG. 14d. For example, the covering member 30 and a silver electrode 85 are immersed in a dilute alkali solution 86, and current is supplied. As shown in FIG. 14e, this forms a main plating film 50b over the metal film 50a produced by strike plating, and the metal film 50a and the plating film 50b can be formed as the heat conduction member 50.

After this, if desired, a translucent heat conduction material film may be formed on just the end face of the light guide member 20 by the above-mentioned lift-off method or the like, thereby forming the heat conduction member shown in FIG. 6s.

There are no restrictions on the thickness of the heat conduction member 50 as long as this member contributes to heat dissipation, but a thickness of about 1 to 100 µm, for example, is favorable.

Embodiments of the present invention will now be described.

Embodiment 1

The light emitting device in this embodiment, as shown in FIGS. 1 and 2a, mainly comprises the light emitting element 10, the light guide member 20, the covering member 30, the wavelength conversion member 40, and the heat conduction member 50. A lens 2 for converging light 1 from the light emitting element 10 is provided on the front face of the light emitting element 10.

An LD composed of a GaN (gallium nitride)-based semiconductor having an emission peak wavelength near 445 nm is used as the light emitting element 10, a quartz SI-type optical fiber (core diameter of 114 µm, cladding diameter of 125 µm) is used as the light guide member 20, the covering member 30 is composed of alumina and had a diameter of 0.7 mm, the wavelength conversion member 40 comprises two kinds of fluorescent material, namely, 0.53 g of $Lu_3Al_5O_{12}$:Ce (emits green light) and 0.2 g of $(Sr,Ca)_2Si_5N_8$:Eu (emits red light), contained in 1.1 g of silicone resin, and AlN (film thickness of 0.1 mm) is used as the heat conduction member 50. The wavelength conversion member 40 is formed by potting.

With this light emitting device, degradation of the wavelength conversion member 40 by heat is greatly reduced as compared to a light emitting device not equipped with the heat conduction member 50. As a result, a reliable light emitting device of high emission output can be obtained.

Embodiment 2

The light emitting device in this embodiment, as shown in FIG. 2e, is the same as in Embodiment 1 except that the heat conduction member 50 was formed from ITO. The ITO was formed by sputtering.

With this light emitting device, degradation of the wavelength conversion member 40 by heat is greatly reduced as compared to a light emitting device not equipped with the heat conduction member 50. As a result, a reliable light emitting device of high emission output can be obtained.

Furthermore, the present invention can be a light emitting device in which two or more of the unit shown in FIG. 1 are combined. In this case, it is preferable for the wavelength conversion member 40 and the heat conduction member 50 both to be constituted by a single member. Also, the light that is ultimately obtained is not limited to white light, and can instead be green light, for instance.

Embodiment 3

With the light emitting device in this embodiment, as shown in FIG. 5m, an LD composed of a GaN (gallium nitride)-based semiconductor having an emission peak wavelength near 405 nm was used as the light emitting element 10, and a heat conduction member 50 composed of ITO (film thickness of 300 nm) was sandwiched between glass and the wavelength conversion member 40. The ITO was formed by sputtering.

The wavelength conversion member 40 was formed by mixing as fluorescent substances 2 g of $Ca_{10}(PO_4)_6Cl_2$:Eu (emits blue light) with 2 g of a liquid mixture of ethyl cellulose and terpineol (weight ratio=12:88), and sintering this mixture for 30 minutes at 80° C., 10 minutes at 200° C., and 1 hour at 500° C. to bake the fluorescent substance. The thickness of the wavelength conversion member 40 was about 500 µm, for example.

Alternatively, the fluorescent substance was a mixture of 10 g of $Ca_{10}(PO_4)_6Cl_2$:Eu (emits blue light), 100 g of isopropyl alcohol, 20 g of alumina sol, and 10 g of acetone, a voltage of 50 V was applied to this, and then the fluorescent substance was dried and electrodeposited to form the wavelength conversion member 40.

For the sake of comparison, a light emitting device was formed by the same method as above, except that no heat conduction member 50 composed of ITO was provided.

Figure 10A:
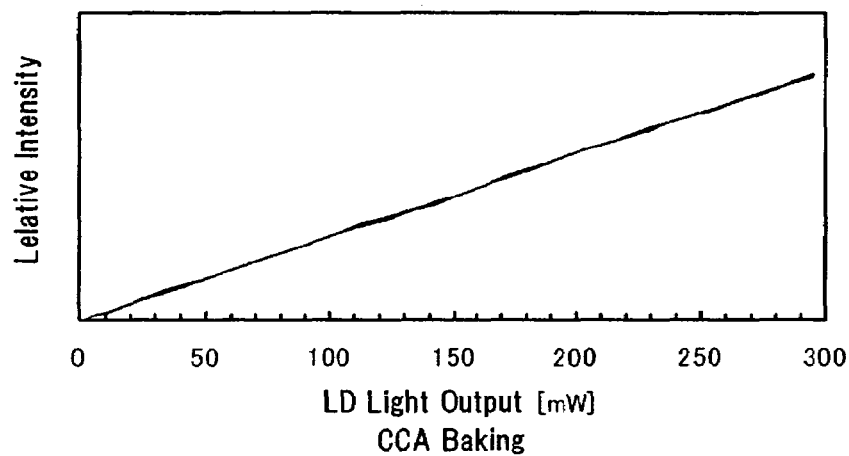
FIGS. 10 to 12 are graphs of the output characteristics in working and comparative examples of the light emitting device of the present invention.
Figure 10B:
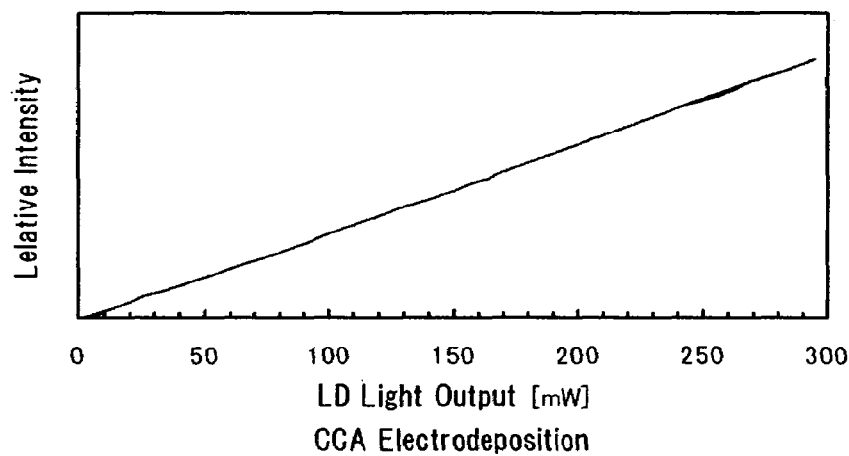
Figure 10C:
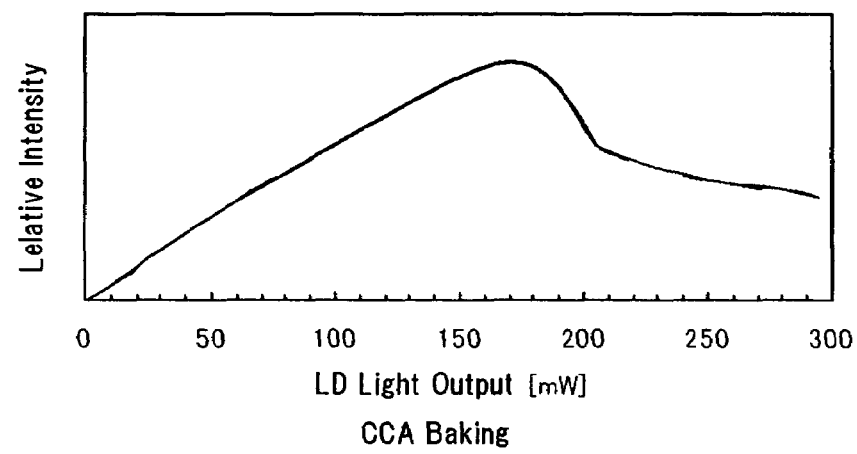

The light output characteristics of the light emitting devices thus obtained were measured, the results of which are given in FIGS. 10a to 10c. FIG. $10_a$ shows the results of baking CCA, FIG. 10b the electrodeposition of CCA, and FIG. 10c the baking of CCA in a comparative example.

It can be seen from FIGS. 10a and 10b that with the light emitting device of this embodiment, providing the heat conduction member 50 yields extremely good linearity between the light output (at the end of the light guide member 20) and the relative intensity of the light flux. In other words, it can be seen that degradation of the wavelength conversion member 40 by heat can be greatly reduced, and that the result is a reliable light emitting device of high light output. Meanwhile, as shown in FIG. 10c, when no heat conduction member 50 was provided, extremely good linearity was not obtained between the light output and the relative intensity of the light flux, and degradation of the wavelength conversion member occurred.

Embodiment 4

With the light emitting device in this embodiment, as shown in FIG. 5m, an LD composed of a GaN (gallium nitride)-based semiconductor having an emission peak wavelength near 445 nm was used as the light emitting element 10, and a heat conduction member 50 composed of ITO (film thickness of 300 nm) was sandwiched between glass and the wavelength conversion member 40. The ITO was formed by sputtering.

The wavelength conversion member 40 was formed from just a fluorescent material by electrodeposition in the same manner as in Embodiment 3, except that $(Y,Gd)_3Al_5O_{12}$:Ce (YAG) was used.

For the sake of comparison, a light emitting device was formed by the same method as above, except that no heat conduction member 50 composed of ITO was provided, and the YAG was baked by the same method as in Embodiment 3.

Figure 11A:
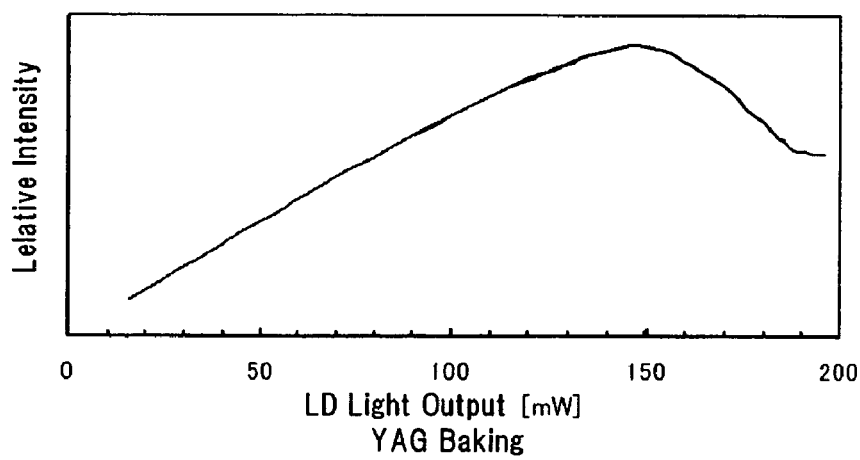
Figure 11B:
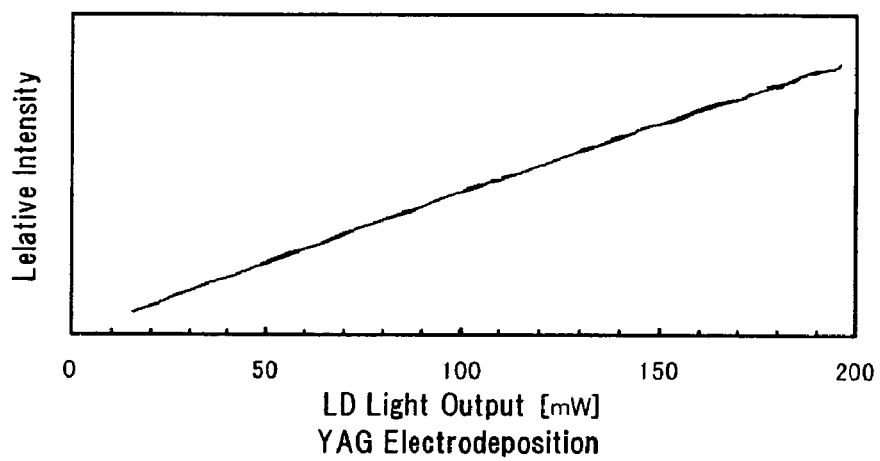

The light output characteristics of the light emitting devices thus obtained were measured, the results of which are given in FIGS. 11a and 11b.

It can be seen from FIG. 11b that with the light emitting device of this embodiment, providing the heat conduction member 50 yields extremely good linearity between the light output and the relative intensity of the light flux. In other words, it can be seen that degradation of the wavelength conversion member 40 by heat can be greatly reduced, and that the result is a reliable light emitting device of high light output. Meanwhile, as shown in FIG. 11a, when no heat conduction member 50 was provided, extremely good linearity was not obtained between the light output and the relative intensity of the light flux, and degradation of the wavelength conversion member occurred.

Embodiment 5

Figure 12A:
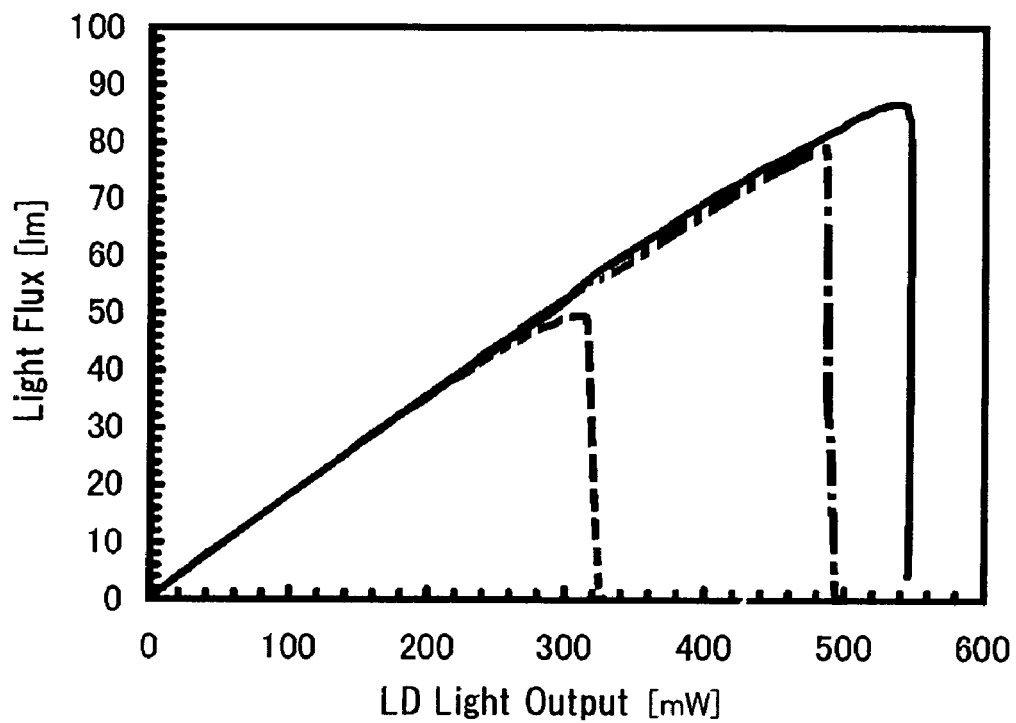
Figure 12B:
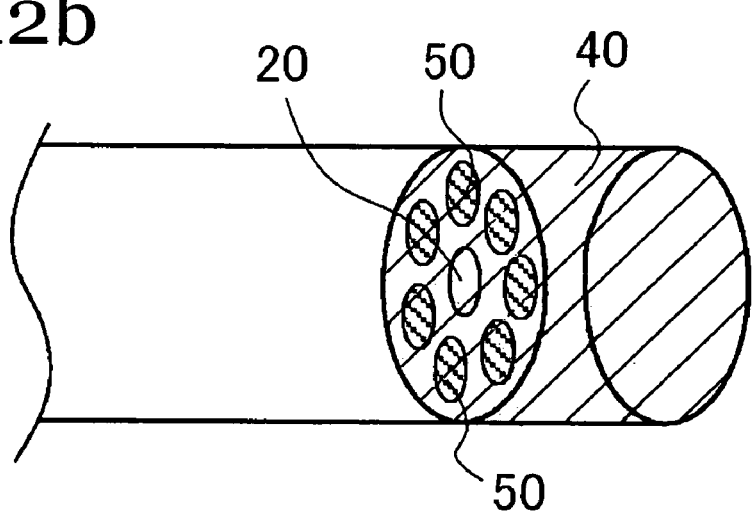

The light emitting device of this embodiment has substantially the same constitution as the light emitting device of Embodiment 1, except that, as a modification of FIG. 5o, a plurality of (such as seven or 14) wire-shaped heat conduction members 50 were provided not protruding into the wavelength conversion member, as shown in FIG. 12b.

The light guide member was an SI-type optical fiber made of silver-plated quartz. The wavelength conversion member 40 was formed by potting, using a mixture of $Lu_3Al_5O_{12}$:Ce (LAG) and $Ca_{0.99}AlSiB_{0.10}N_{3.1}$:$Eu_{0.01}$ (CASBN) in a silicone resin.

The wire-shaped heat conduction members 50 consisted of tin-plated soft steel with a diameter of 160 μm.

For the sake of comparison, a light emitting device was formed with the same constitution as above, except that no wire-shaped heat conduction members 50 were provided.

The light output characteristics of the light emitting devices thus obtained were measured, the results of which are given in FIG. 12a.

It can be seen from FIG. 12a that as the number of wire-shaped heat conduction members was increased from zero (dashed line) to seven (one-dot chain line) and then to 14 (solid line), the degradation of the wavelength conversion member 40 by heat was greatly reduced, and as a result a larger light output could be obtained.

The light emitting device of the present invention can be utilized in indicators, displays, and various kinds of lighting, such as lighting installed in automobiles. It can also be utilized in fiber scopes that allow illumination of narrow gaps and dark spaces, in endoscopes for imaging the inside of the body, and so forth.

This application claims priority to Japanese Patent Application Nos. 2005-172220 and 2006-129332. The entire disclosure of Japanese Patent Application Nos. 2005-172220 and 2006-129332 are hereby incorporated herein by reference.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing description of the embodiments according to the present invention are provided for illustration only, and not for the purpose of limiting the invention as defined by the appended claims and their equivalents.

What is claimed is:

1. A light emitting device, comprising at least:
   a light emitting element;
   a wavelength conversion member for converting the wavelength of light from the light emitting element;
   a bendable light guide member for guiding light from the light emitting element to the wavelength conversion member; and
   a heat conduction member that is thermally connected to the wavelength conversion member.

2. The light emitting device according to claim 1, further comprising a covering member that covers at least part of the side face of the light guide member,
   wherein the covering member and the wavelength conversion member are thermally connected via the heat conduction member.

3. The light emitting element according to claim 1, wherein the wavelength conversion member is made up of at least a translucent member and a fluorescent material.

4. The light emitting device according to claim 1, wherein the light emitting element is a laser diode, and
   the light guide member is an optical fiber.

5. The light emitting device according to claim 1, wherein the heat conduction member is composed of a material having a thermal conductivity of at least 0.1 w/m·k.

6. The light emitting device according to claim 1, wherein the covering member is composed of an electroconductive material, and the heat conduction member is composed of a plating film formed on all or part of the outer surface of the covering member.

* * * * *

UNITED STATES PATENT AND TRADEMARK OFFICE
CERTIFICATE OF CORRECTION

PATENT NO.       : 7,422,356 B2                                    Page 1 of 1
APPLICATION NO.  : 11/449719
DATED            : September 9, 2008
INVENTOR(S)      : Atsutomo Hama et al.

It is certified that error appears in the above-identified patent and that said Letters Patent is hereby corrected as shown below:

<u>On the cover page,</u>
change the inventors' residence information listed in (75) Inventors, from "(75)   Inventors:     Atsutomo Hama, Anan (JP);

Yukihiro Hayashi, Anan (JP)"

to

-- (75)   Inventors:     Atsutomo Hama, Komatsushima-shi (JP);

Yukihiro Hayashi, Tokushima-shi (JP) --

Signed and Sealed this

Fourteenth Day of October, 2008

JON W. DUDAS
*Director of the United States Patent and Trademark Office*